US012544602B2

(12) United States Patent
Barbeau et al.

(10) Patent No.: US 12,544,602 B2
(45) Date of Patent: Feb. 10, 2026

(54) FIREFIGHTER PROTECTIVE HOOD AND GLOVES WITH REGENERATED CELLULOSE FIBER

(71) Applicant: INNOTEX INC., Richmond (CA)

(72) Inventors: Claude Barbeau, St-Bruno (CA); France Lozier, Montreal (CA); Stéphane Rousse, Point-Claire (CA)

(73) Assignee: INNOTEX INC. (CA)

( * ) Notice: Subject to any disclaimer, the term of this patent is extended or adjusted under 35 U.S.C. 154(b) by 0 days.

(21) Appl. No.: 15/874,486

(22) Filed: Jan. 18, 2018

(65) Prior Publication Data

US 2018/0207453 A1 Jul. 26, 2018

Related U.S. Application Data

(60) Provisional application No. 62/447,698, filed on Jan. 18, 2017.

(51) Int. Cl.
*A62B 17/00* (2006.01)
*A41D 19/015* (2006.01)
(Continued)

(52) U.S. Cl.
CPC ...... *A62B 17/003* (2013.01); *A41D 19/01529* (2013.01); *A41D 31/085* (2019.02);
(Continued)

(58) Field of Classification Search
CPC ....... A62B 17/003; A62B 17/04; A62B 18/00; A62B 18/02; A62B 18/04; A42B 3/00;
(Continued)

(56) References Cited

U.S. PATENT DOCUMENTS

| | | | | |
|---|---|---|---|---|
| 544,832 A * | 8/1895 | Senior | .................... | A62B 17/04 128/201.23 |
| 2,240,751 A * | 5/1941 | Boesger | ................. | A62B 18/04 128/201.23 |

(Continued)

OTHER PUBLICATIONS

Office Action received for Canadian Patent Application No. 2992242, mailed on Aug. 5, 2024, 5 pages.

*Primary Examiner* — Khaled Annis
*Assistant Examiner* — Dakota Marin
(74) *Attorney, Agent, or Firm* — Dilworth IP, LLC

(57) ABSTRACT

A firefighter protective hood that protects the coat/helmet/self-contained breathing apparatus facepiece interface area of a user, and a firefighter protective glove that protects the hand and wrist of the user are provided. The firefighter protective hood and glove respectively include a hood-shaped structure and a glove-shape structure. The hood-shaped structure and the glove-shaped structures each include a body-contacting layer made of a fabric of flame-retardant regenerated cellulose fibers. The structure and composition of the body-contacting layer promote comfort of the user and evaporative cooling. Outer layer(s) extend outwardly over the body-contacting layer and act as thermal and mechanical barriers. The combination of such layers allows maintaining relatively high perspiration transmission and evaporation, and substantially good thermal and mechanical properties.

23 Claims, 10 Drawing Sheets

(51) Int. Cl.

| | |
|---|---|
| ***A41D 31/08*** | (2019.01) |
| ***A42B 1/046*** | (2021.01) |
| ***A42B 3/10*** | (2006.01) |
| ***A62B 17/04*** | (2006.01) |
| *A42B 3/00* | (2006.01) |
| *A42B 3/06* | (2006.01) |
| *A61F 9/06* | (2006.01) |
| *A62B 18/00* | (2006.01) |
| *A62B 18/02* | (2006.01) |
| *A62B 18/04* | (2006.01) |

(52) U.S. Cl.

CPC .............. *A42B 1/046* (2013.01); *A42B 3/105* (2013.01); *A62B 17/04* (2013.01); *A41D 2200/20* (2013.01); *A41D 2600/20* (2013.01); *A42B 3/00* (2013.01); *A42B 3/061* (2013.01); *A42B 3/063* (2013.01); *A42B 3/10* (2013.01); *A61F 9/06* (2013.01); *A62B 18/00* (2013.01); *A62B 18/02* (2013.01); *A62B 18/04* (2013.01); *B32B 2307/3065* (2013.01); *B32B 2307/7246* (2013.01)

(58) Field of Classification Search

CPC ........... A42B 3/063; A42B 3/10; A42B 3/105; A42B 3/061; A61F 9/06; A41D 2200/20; A41D 19/01529; B32B 2307/3065

USPC ............................................................... 2/7, 5

See application file for complete search history.

(56) References Cited

U.S. PATENT DOCUMENTS

| | | | | | |
|---|---|---|---|---|---|
| 3,535,706 | A * | 10/1970 | Aileo | A42B 3/003 | 2/5 |
| 4,473,614 | A * | 9/1984 | Hockmeyer | A62B 17/001 | 442/238 |
| 4,972,520 | A | 11/1990 | Grilliot et al. | | |
| 5,090,054 | A | 2/1992 | Grilliot et al. | | |
| 5,221,572 | A * | 6/1993 | Meunier | A62D 5/00 | 442/184 |
| 5,499,663 | A | 3/1996 | Barbeau et al. | | |
| 5,628,065 | A * | 5/1997 | Austin | A42B 1/048 | 2/202 |
| 5,873,132 | A | 2/1999 | Grilliot et al. | | |
| 6,662,375 | B2 | 12/2003 | Lewis | | |
| 6,691,314 | B1 * | 2/2004 | Grilliot | A62B 17/04 | 128/201.25 |
| 6,763,835 | B1 * | 7/2004 | Grove | A62B 17/04 | 128/201.25 |
| 6,829,784 | B2 * | 12/2004 | Austin | A42B 3/105 | 2/202 |
| 6,996,360 | B2 | 2/2006 | Koga et al. | | |
| 8,225,428 | B2 | 7/2012 | Grilliot et al. | | |
| 8,613,113 | B1 * | 12/2013 | Resnick | A62B 17/04 | 128/201.23 |
| 8,728,217 | B2 * | 5/2014 | Velpari | B01D 39/083 | 96/134 |
| 2003/0204895 | A1 | 11/2003 | Grilliot et al. | | |
| 2003/0228812 | A1 * | 12/2003 | Stanhope | D03D 1/0041 | 442/49 |
| 2004/0198125 | A1 * | 10/2004 | Mater | D04H 1/43828 | 442/394 |
| 2004/0259446 | A1 * | 12/2004 | Jain | A62D 5/00 | 442/59 |
| 2005/0014432 | A1 * | 1/2005 | Jain | A41D 31/02 | 442/76 |
| 2005/0193472 | A1 * | 9/2005 | Courtney | A62B 17/04 | 2/202 |
| 2008/0196146 | A1 | 8/2008 | Grilliot et al. | | |
| 2009/0117367 | A1 * | 5/2009 | Stone | B32B 5/32 | 428/315.5 |
| 2009/0178186 | A1 * | 7/2009 | Truesdale | D03D 15/12 | 2/455 |
| 2009/0205116 | A1 * | 8/2009 | Stone | A01N 25/10 | 2/455 |
| 2010/0138983 | A1 * | 6/2010 | Kim | B32B 5/26 | 2/458 |
| 2010/0287680 | A1 * | 11/2010 | Johnson | A41D 31/24 | 2/87 |
| 2012/0174296 | A1 * | 7/2012 | Martin | A62B 17/006 | 2/457 |
| 2014/0209331 | A1 * | 7/2014 | Burkett | A62C 2/06 | 169/46 |
| 2015/0121598 | A1 | 5/2015 | Mathews et al. | | |
| 2016/0095359 | A1 * | 4/2016 | Fox | A41D 3/005 | 2/84 |
| 2017/0127748 | A1 * | 5/2017 | Sethumadhavan | A42B 3/063 | |
| 2017/0130372 | A1 * | 5/2017 | Underwood | A41D 31/08 | |
| 2017/0173370 | A1 * | 6/2017 | Underwood | A41D 31/085 | |
| 2017/0175302 | A1 * | 6/2017 | Habicht | D02G 3/443 | |
| 2017/0188651 | A1 * | 7/2017 | Brust | A42B 1/045 | |

* cited by examiner

FIREFIGHTER PROTECTIVE HOOD AND GLOVES WITH REGENERATED CELLULOSE FIBER

TECHNICAL FIELD

The technical field generally relates to protective hoods and gloves part of the protective ensemble of a firefighter.

BACKGROUND

According to the National Fire Protection Association (NFPA), a firefighter protective hood is an interface element of the firefighter protective ensemble that provides limited protection to the coat/helmet and/or self-containing breathing apparatus (SCBA) face-piece interface area. A typical firefighter protective hood comprises one or more functional layer(s) of flame-resistant materials. The functional layer(s) are typically made of knit material(s) such as: flame-resistant spun yarns of meta-aramids (ex. Nomex®), para-aramids (ex. Kevlar®), polybenzimidazole (PBI®), melamine (Basofil®), polyamide (P84®), flame-resistant regenerated cellulose (Rayon, Viscose, modal, Lenzing® modal or lyocell), polyacrylonitrile (PAN), carbon or various combinations thereof.

For example, known to the Applicant are the following US patents and patent applications: U.S. Pat. Nos. 4,972,520; 5,090,054; 5,499,663; 5,873,132; 6,662,375; 6,829,784; 6,996,360; 8,225,428; 2003/0204895, and 2008/0196146. They exemplify protective hoods as disclosed in the prior art. For example, the size of the aperture for the face or the use of varying weights of fabric to provide different levels of thermal protection are explored variations of typical protective hoods as currently manufactured and used for firefighting activities.

More particularly, US patent application 2003/0204895 discloses a protective hood consisting of multiple layers. One of the multiple layers, more particularly the one that is the closest to the skin of the firefighter, is a vapor-permeable membrane.

Although protective hoods from the prior art meet all the mandatory performance requirements of the National Fire Protection Standard (NFPA 1971), this element of typical firefighter protective ensembles as actually available on the market present drawbacks, such as lack of comfort for the wearer.

Firefighter gloves also suffer from the abovementioned limitations, and are hence associated with challenges that are similar to the ones described above with respect to the firefighter protective hood.

Thus, it would be particularly useful to be able to provide improved firefighter protective hoods or gloves which, by virtue of its design and components, would be able to overcome or at least minimize some of the known drawbacks associated with conventional firefighter protective hoods or gloves.

SUMMARY

In accordance with one aspect, there is provided a firefighter protective hood including a hood-shaped structure. The hood-shaped structure includes a plurality of superimposed layers, including: a body-contacting layer made of a fabric of multifilament flame-retardant cellulose fibers, and at least one outer layer extending over at least a portion of the body-contacting layer. The body-contacting layer is made of a fabric of multifilament flame-retardant cellulose fibers. The body-contacting layer define an innermost one of the plurality of superimposed layers; The at least one outer layer extends over at least a portion of the body-contacting layer.

In some embodiments, the multifilament flame-retardant cellulose fibers are rayon fibers.

In some embodiments, the rayon fibers are viscose fibers.

In some embodiments, the at least one outer layer is made from a material selected from the group consisting of: spun yarns, multifilament yarns and combinations of spun and multifilament yarns.

In some embodiments, wherein the at least one outer layer comprises a particulate barrier.

In some embodiments, the particulate barrier is laminated with the body contacting layer.

In some embodiments, the particulate barrier is made of expanded polytetrafluoroethylene.

In some embodiments, the particulate barrier is made of meta-aramid nanofibers.

In some embodiments, the firefighter protective hood is compliant to NFPA 1971 (2013 edition) Standard on Protective Ensembles for Structural Fire Fighting and Proximity Fire Fighting.

In accordance with another aspect, there is provided a firefighter protective glove including a glove-shaped structure. The glove-shaped structure includes a plurality of superimposed layers, including: a body-contacting layer made of a fabric of multifilament flame-retardant cellulose fibers, a moisture barrier and an outer shell extending over the moisture particulate barrier. The body-contacting layer defines an innermost one of the plurality of superimposed layers. The outer shell defines an outermost one of the plurality of superimposed layers.

In some embodiments, the flame-retardant cellulose fibers are rayon fibers.

In some embodiments, the rayon fibers are viscose fibers.

In some embodiments, the glove-shaped structure includes a palm side portion and a back-hand side portion, and at least one of the palm side portion and the back-hand portion comprises the plurality of superimposed layers.

In some embodiments, at least one of the moisture barrier and the outer shell is made from a material selected from the group consisting of: spun yarns, multifilament yarns and combinations of spun and multifilament yarns.

In some embodiments, the moisture barrier is laminated with the body-contacting layer.

In some embodiments, the particulate barrier is made of expanded polytetrafluoroethylene.

In some embodiments, the particulate barrier is made of polyurethane.

In some embodiments, the outer shell is made of a leather.

In some embodiments, the firefighter protective glove is compliant to NFPA 1971 (2013 edition) Standard on Protective Ensembles for Structural Fire Fighting and Proximity Fire Fighting.

In accordance with another aspect, there is provided a firefighter protective hood that provides protection to the coat/helmet/self-contained breathing apparatus facepiece interface area. The firefighter protective hood comprises a body-contacting layer made of a fabric of flame-resistant regenerated cellulose fibers.

In an embodiment, the body-contacting layer is made of a fabric of multifilament flame-resistant regenerated cellulose fibers.

In an embodiment, the cellulose fiber is a rayon fiber.

In an embodiment, the rayon fiber is a viscose fiber.

In an embodiment, the body-contacting layer is made of a knitted fabric.

In an embodiment, the body-contacting layer is made of a woven fabric.

In an embodiment, the firefighter protective hood comprises a plurality of superimposed layers and the body-contacting layer defines an innermost one of the plurality of superimposed layers.

In an embodiment, the plurality of superimposed layers comprises at least one outer layers and the at least one outer layers extends outwardly of the body-contacting layer.

In an embodiment, the at least one outer layer is made from a material selected from the group consisting of: spun yarns, multifilament yarns and combinations of spun and multifilament yarns.

In an embodiment, the at least one outer layer comprises a semi-permeable particulate barrier.

In an embodiment, the semi-permeable particulate barrier is made of expanded polytetrafluoroethylene or meta-aramid nanofiber (NOMEX®).

In an embodiment, the semi-permeable particulate barrier is laminated with the innermost one of said plurality of layers.

In an embodiment, at least one of the at least one outer layer is made of a knitted fabric.

In an embodiment, at least one of the at least one outer layer is made of a woven fabric.

In an embodiment, the firefighter protective hood is compliant to NFPA 1971 (2013 edition) Standard on Protective Ensembles for Structural Fire Fighting and Proximity Fire Fighting.

In accordance with another aspect, there is provided a firefighter protective glove that provides protection to the hand and wrist. The firefighter protective glove comprises a body-contacting layer made of a fabric of flame-resistant regenerated cellulose fibers.

In an embodiment, the body-contacting layer is made of a fabric of multifilament flame-resistant regenerated cellulose fibers.

In an embodiment, the cellulose fiber is a rayon fiber.

In an embodiment, the rayon fiber is a viscose fiber.

In an embodiment, the body-contacting layer is made of a knitted fabric.

In an embodiment, the body-contacting layer is made of a woven fabric.

In an embodiment, the firefighter protective glove comprises a palm side portion and a back-hand side portion.

In an embodiment, at least one of the palm side portion and the back-hand portion comprises a plurality of superimposed layers and the body-contacting layer defines an innermost one of the plurality of superimposed layers.

In an embodiment, the palm side portion and the back-hand portion each comprises a plurality of superimposed layers and the body-contacting layer defines an innermost one of said plurality of superimposed layers.

In an embodiment, the plurality of superimposed layers comprises at least one outer layers and the at least one outer layer extends outwardly of the body-contacting layer.

In an embodiment, the at least one outer layer is made from a material selected from the group consisting of: spun yarns, multifilament yarns and combinations of spun and multifilament yarns.

In an embodiment, the at least one outer layer comprises a semi-permeable particulate barrier.

In an embodiment, the semi-permeable particulate barrier is made of expanded polytetrafluoroethylene or polyurethane.

In an embodiment, the semi-permeable particulate barrier is laminated with the innermost one of the plurality of layers.

In an embodiment, at least one of the at least one outer layer is made of a knitted fabric.

In an embodiment, at least one of the at least one outer layer is made of a woven fabric.

In an embodiment, at least one of the at least one outer layer is made of a leather.

In an embodiment, the firefighter protective glove is compliant to NFPA 1971 (2013 edition) Standard on Protective Ensembles for Structural Fire Fighting and Proximity Fire Fighting.

Other features and advantages of the invention will be better understood upon reading of embodiments thereof with reference to the appended drawings.

DETAILED DESCRIPTION

Figure 1:
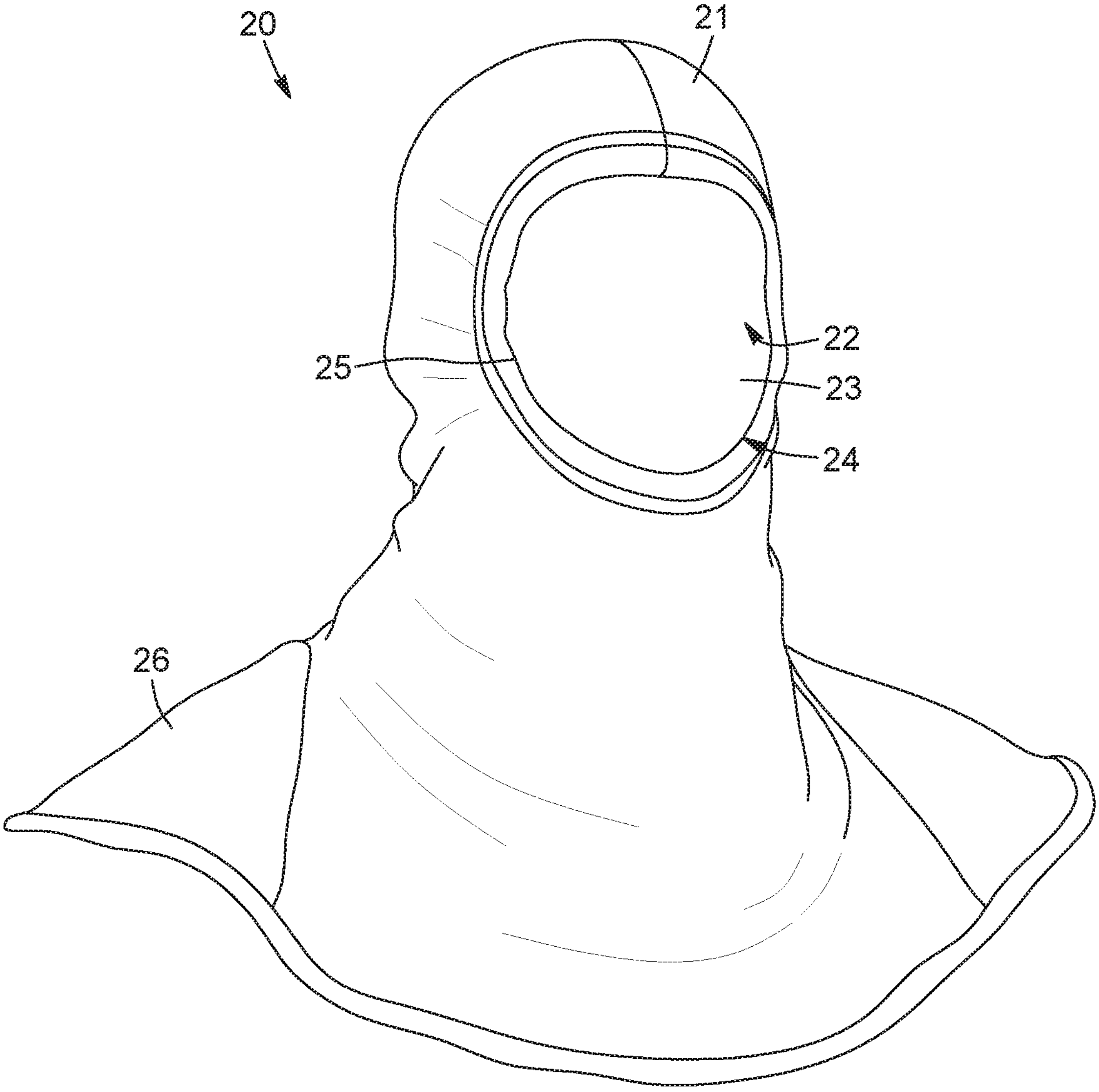
FIG. 1 shows a firefighter protective hood according to a possible embodiment.

In the following description, similar features in the drawings have been given similar reference numerals. In order to not unduly encumber the figures, some elements may not be indicated on some figures if they were already mentioned in preceding figures. It should also be understood herein that the elements of the drawings are not necessarily drawn to scale and that the emphasis is instead being placed upon clearly illustrating the elements and structures of the present embodiments.

Moreover, it will be appreciated that positional descriptions such as “top”, “bottom”, “under”, “left”, “right”, “front”, “rear”, “adjacent”, “opposite”, “innermost”, “outermost”, “inner”, “outer”, “internal”, “external”, “superimposed”, “body-contacting” and the like should, unless otherwise indicated, be taken in the context of the figures and should not be considered limiting.

The present description relates to components of a firefighter protective hood or glove.

Elements of a firefighter protective ensemble are for example as defined by the National Fire Protection Association in NFPA 1976: Standard on Protective Ensemble for Proximity Fire Fighting, 2000 Edition. It should be understood that the terms "firefighter protective ensemble", "protective ensemble" and "ensemble" refer to multiple elements of compliant protective clothing that, when worn together can reduce, but not necessarily eliminate, the health and safety risks of emergency incident operations. Examples of compliant protective clothing comprise, but are not limited to: a coat, a pant; a coverall, a footwear, garment, glove, helmet, hood; offering protection against heat and flame, chemical, biological, radiological and nuclear terrorism agent or other hazards commonly encountered in firefighting duties.

In the present disclosure, the following terminology and expressions relating to the may be used:

1) The terms "structural fire fighting protective garments", "protective garments" and "garments" refer to the coat, trouser, and coverall elements of the protective ensemble;
2) The terms "structural fire fighting protective glove", "protective glove" and "glove" refer to an element of the protective ensemble that provides protection to the hand and wrist;
3) The terms "structural fire fighting protective hood", "protective hood" and "hood" refer to the interface element of the protective ensemble that provides limited protection to the coat/helmet/SCBA (self-contained breathing apparatus) facepiece interface area;
4) The term "fabric" refers specifically to a woven or knitted material, and more generally to flexible materials comprising a network of natural fibers, artificial fibers or combination thereof. Unless otherwise specified, the description of the fabric is applicable to both woven and knitted materials, but also to materials that will be later introduced and described;
5) The term "yarn" is a generic term referring to continuous strand of spun fiber, filament or any other materials having a form that is suitable for knitting, weaving, braiding, intertwining or the like to form a textile fabric; and
6) The term "flame-resistant" will be understood as the property of a material (e.g. solid, liquid or gas) or design (e.g. a structure) to resist the effects of any fire to which the material or structure can be expected to be subjected, but will also encompass the term "flame-retardant", namely the property of a material (e.g. solid, liquid or gas) to inhibit combustion. For this reason, the term "flame-resistant", "flame-retardant", "fire-retardant" and "fire-retardant" will be used interchangeably;
7) The term "multifilament" refers to a yarn comprising more than one filament that runs the whole length of the yarn;
8) The term "cellulose" is understood to mean an inert carbohydrate, the main constituent of the cell walls of plants and of wood, cotton, hemp, paper, or the like. For example, the term "cellulose" may be understood as an organic compound with the formula $(C_6H_{10}O_5)_n$, i.e., a polysaccharide comprising a linear chain made of several hundred to many thousands of $\beta(1\rightarrow4)$ linked D-glucose units;
9) The term "regenerated" is understood to mean the conversion of natural cellulose to a soluble cellulosic derivative, and subsequent regeneration into a continuous filament yarn by extrusion; and
10) The terms "rayon fibers" and "viscose fibers" are understood to mean filament or spun fibers made of certain types of regenerated cellulose, that may for example be used to produce the knitted or woven fabric.

The firefighter protective ensembles and related compliant protective elements (also referred to as "clothing") are particularly useful in the activities of fire suppression, property conservations (e.g. building, vehicles, or the like) and related rescue tasks. Although such ensembles and clothing may be particularly useful for firefighters, they may also be aimed at other emergency worker, such as paramedics and police officers.

Firefighter Protective Hood

Referring to FIG. 1, an embodiment of a firefighter protective hood 20 is shown.

The firefighter protective hood 20 includes a hood-shaped structure 21. Generally described, the hood-shaped structure 21 preferably has a shape and dimensions designed to substantially cover the wearer's head, face, neck and shoulders regions or at least portions thereof.

According to one possible embodiment, such as the one illustrated in FIG. 1, the hood-shaped structure 21 notably comprises one face opening 24. The face opening 24 may be of such dimensions that it allows the user's face or a portion of the user's face to protrude from the protective hood 21 where wore by the user. In some implementations, the face opening 24 may fit snugly around the facepiece of an SCBA (self-contained breathing apparatus), as well as around the neck of the user. The face opening 24 may also be reinforced along a portion or an entirety of its perimeter 25 using knitting, weaving, stitching, binding or the like. The perimeter 25 could alternatively comprise a band of elastic and/or resilient material to provide comfort to the user. Dimensions and materials used for reinforcing the perimeter 25 may be selected such that the face opening 24 remains substantially in place when wore, and so to relatively tightly fit around a portion of the user's face.

Alternatively, the hood-shaped structure 21 could comprise a plurality of face openings defining corresponding eye, mouth and/or nose openings. In such a configuration, the hood-shaped structure 21 may be useful to different users and/or first responders that would not specifically need to use a SCBA. For example, the hood-shaped structure may comprise two openings (e.g., one for each eye of the user), three openings (e.g., one for each eye and one for the mouth of the user), or even more openings in order to accommodate different users.

Figure 2:
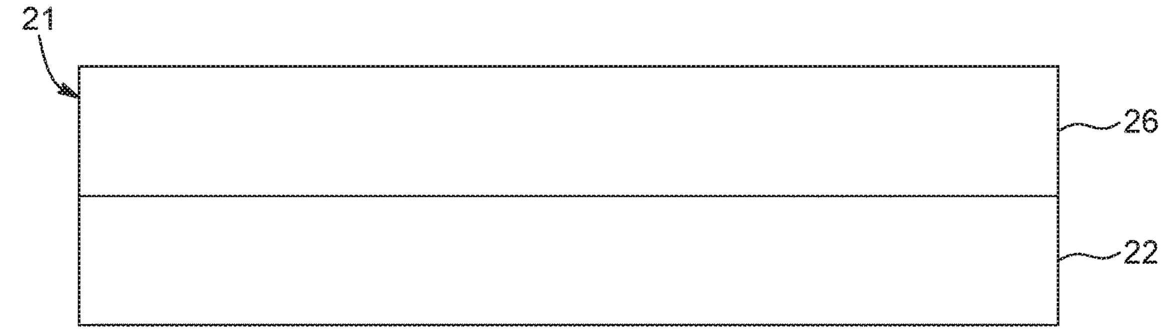
FIG. 2 shows a schematic cross-sectional view of a hood-shaped structure according to a possible embodiment.

Now turning to FIG. 2, a cross-section view of an embodiment of the hood-shaped structure 21 is illustrated. In this embodiment, the hood-shaped structure 21 includes a plurality of superimposed layers (herein referred to as "the superimposed layers"). As it will be described in more detail below, the plurality of superimposed layers includes a body-contacting layer 22 and at least one outer extending layer (numbered 26 when there is only one outer layer, and being respectively numbered 26*a*, 26*b*, . . . , 26*n* in the case of n outer layers). Each layer of the hood-shaped structure 21 (i.e., the body-contacting layer and the at least one outer layer 26) is made of a fabric. By way of example, the hood-shaped structure 21 depicted in FIG. 2 includes a body-contacting layer 22 and one outer layer 26.

Generally described, the body-contacting layer 22 is made of a fabric of multifilament flame-retardant cellulose fibers. The flame-retardant cellulose fiber may for example be embodied by Rayon, Viscose, modal, Lenzing® modal or lyocell fibers, or the like. The fabric forming the body-contacting layer 22 preferably has the required structural and mechanical properties allowing perspiration or any other liquid(s) produced by the user to be evaporated. Surface area, thickness, types of material and/or size of perforations (i.e., density of the yarns) of the fabric are only some of the structural and mechanical properties that may promote the evaporative cooling. The above listed fabric examples allow the body-contacting layer 22 to better slide on a user's skin (i.e., may reduce what is known as the "dynamic load" of the protective hood 20).

The body-contacting layer 22 is preferably 100% made of flame-retardant regenerated multifilament cellulose fibers. It is to be noted that a small amount of spun fibers could be added to the multifilament cellulose fibers. For example, the body-contacting layer 22 could be 75% made of flame-retardant regenerated multifilament. That is, the body-contacting layer 22 could include up to about 25% of other constituents, for example and without being limitative, meta-aramids (e.g., Nomex®), para-aramids (e.g., Kevlar®), polybenzimidazole (PBI®), melamine (e.g., Basofil®), polyamide (e.g., P84®), polyacrylonitrile (PAN), or carbon fibers. It will be readily understood that while a small amount (e.g., 25% or less) of spun fibers could be added to the multifilament cellulose fibers, the composition of the body-contacting layer 22 is such that it allows to keep the benefits of the multifilament fibers.

In the context of the present disclosure, a body-contacting layer including up to about 25% of other constituents than the flame-retardant filament cellulose fibers may fall within the scope of the expression "a body-contacting layer made of a fabric of flame-retardant cellulose fibers", as explained above.

In some variants, the cellulose fiber forming the body-contacting layer 22 is a rayon fiber, and the rayon fiber is a viscose fiber. As it has been previously mentioned, the fabric forming the body-contacting layer 22 can be made of knitted and/or woven fabric. It is also to be noted that the fabric forming the body-contacting layer 22 could not only be knitted and/or woven, but could also be intertwined, braided, or obtained by any other means and methods allowing creating fabric from multiple filaments.

As mentioned above, the fabric of flame-retardant cellulose fibers includes multifilament fibers or yarns. For example, the body-contacting layer 22 could be a knitted fabric formed of 100% multifilament cellulose fibers, the cellulose fibers being selected from the list of materials which have been previously presented. It is to be noted that the multifilament cellulose fibers can be multifilament regenerated cellulose fibers.

The body-contacting layer 22 defines an innermost one of the plurality of superimposed layers, which means that the body-contacting layer 22 is the layer of the protective hood 20 that is closer to the body of the wearer when wore. The body-contacting layer 22 may be directly or indirectly in contact with the body of the wearer, and may cover at least portion(s) of specific area of the skin and/or body of the user that need to be mechanically and thermally protected, and allows evaporative cooling (i.e., promotes wicking of the sweat).

The body-contacting layer 22 is preferably in direct contact with a substantial portion of the skin, facial hair and/or hair of the user in the areas typically covered by a firefighter hood. However, it will be readily understood that some portions of the body-contacting layer 22 could be in indirect contact with the body of the user, meaning that there may be an intermediate layer between the body-contacting layer 22 (or portion(s) thereof) and skin and/or body of the user. For example, the body-contacting layer 22 may be in contact with clothes, elements the firefighter protective ensemble and/or any other piece of equipment that may be worn by the user.

As it has been previously mentioned, the hood-shaped structure 21 includes at least one outer layer 26 (also referred to as the outer layer(s)) extending over at least a portion of the body-contacting layer 22. Because the body-contacting layer 22 is the innermost one of the plurality of superimposed layers, the outer layer 26 can be said to extend outwardly of the body-contacting layer 22 and defines an outermost of the superimposed layers.

In some embodiments, the outer layers 26 extend over an entirety of the body-contacting layer 22, i.e., the outer layers 26 and the body-contacting layer 22 form a stack of materials over their respective surface area.

Alternatively, the outer layers 26 could extend over a portion of the body-contacting layer 22, so as to expose predetermined areas of the body-contacting layer 22, for example for better cooling of high metabolic heat in specific regions of the user's body.

The body-contacting layer 22 and the outer layers 26 have different, yet complementary functionalities. Indeed, the structure and composition of the body-contacting layer 22 are such that they provide comfort to the user and evaporative cooling, while the outer layers 26 notably act as thermal and mechanical barriers. Moreover, the body-contacting layer 22 promotes air circulation and may for example be porous. The outer layers 26 promotes mechanical and thermal resistance, and may further comprise air-permeable knits. The combination of such layers allows maintaining relatively high perspiration transmission and evaporation, while exhibiting substantially good thermal and mechanical properties.

In some embodiments, the outer layers 26 is made from a material selected from spun yarns, multifilament yarns, or various combinations of spun and multifilament yarns. Alternatively, the outer layers 26 could be made of knitted multifilament yarns made from any other flame-retardant cellulosic fibers.

In general, at least one of the outer layers 26 is made of a knitted fabric, selected from the group including, for example and without being limitative: aramid, meta-aramid, para-aramid or any other flame and/or heat-resistant synthetic fiber. Alternatively, the at least one of the outer layers 26 is made of a woven fabric made of the previously listed materials. In some implementations, each of the outer layers 26 may be made of or include, for example and without being limitative, flame-retardant yarns such as, and without being limitative, meta-aramids (e.g., Nomex®), para-aramids (e.g., Kevlar®), polybenzimidazole (e.g., PBI®), melamine (e.g., Basofil®), polyamide (e.g., P84®), flame-retardant regenerated cellulose (e.g., Rayon, Viscose, modal, Lenzing® modal or lyocell fibers), polyacrylonitrile (e.g., PAN), carbon, or various combinations thereof.

Figure 3:
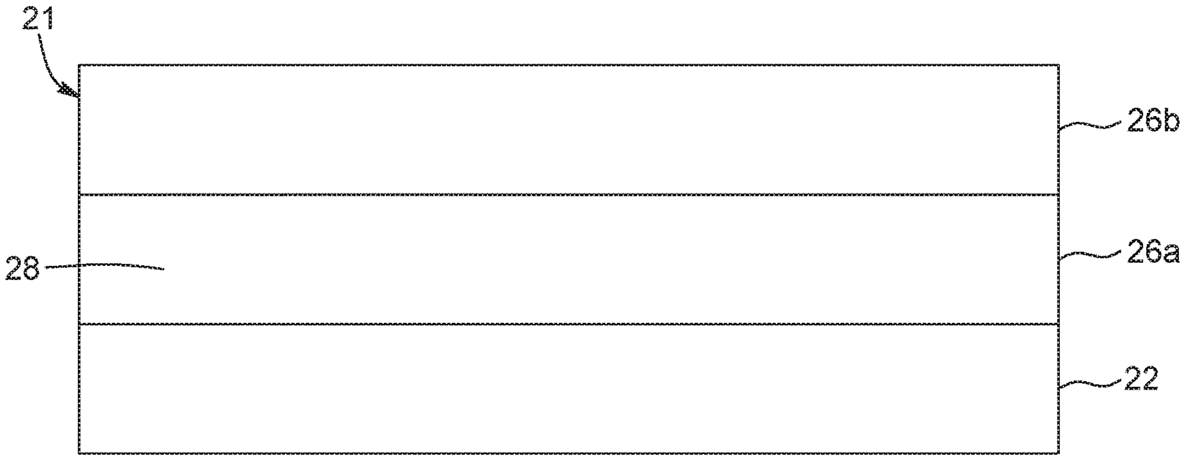
FIG. 3 shows a schematic cross-sectional view of a hood-shaped structure according to another possible embodiment.

In some embodiments, such as the one illustrated in FIG. 3, the outer layers 26*a,b* comprise a semi-permeable particulate barrier 28. In the following, the semi-permeable particulate barrier 28 may also simply referred to as a "particulate barrier 28". In the illustrated embodiment, the outer layer 26*b* defines an outermost layer, and the semi-permeable particulate barrier 28, which is defined by the outer layer 26*a*, extends between the body-contacting layer 22 and the outer layer 26*b*. The semi-permeable particulate barrier 28 can be a piece of fabric, plastic, polymer, combinations thereof, or any other material having the structural properties to ensure passage of only certain or a portion of certain type of molecule(s) and/or particulates.

In some implementations, the semi-permeable particulate barrier 28 is laminated with the body-contacting layer 22.

In some embodiments, the semi-permeable particulate barrier 28 is made of expanded polytetrafluoroethylene (ePTFE). Alternatively, the semi-permeable particulate barrier 28 could be made of meta-aramid nanofibers (e.g., Nomex®). Optionally, the semi-permeable particulate barrier 28 may be a membrane.

In some embodiments, the semi-permeable particulate barrier 28 may be impermeable to particulate(s) having a diameter of about or greater than 1 micrometer, while being permeable to water and/or water vapors (also referred to "water/air permeability"). It will be understood that the function of the semi-permeable particulate barrier 28 is to promote air circulation and evaporative cooling, while blocking at least some or every particulate that may be harmful to the user, such as cancerous or toxic particulates.

In one embodiment, the semi-permeable particulate barrier 28 is laminated to the body-contacting layer 22 or to one of the outer layers 26. As such, the semi-permeable particulate barrier 28 is stacked ("sandwiched") between the body-contacting layer 22 and one of the outer layer 26. Alternatively, the semi-permeable particulate barrier 28 could be affixed to the body-contacting layer 22 using appropriate affixing means, such as glue, stitches, staples, laminated, rivet, combination thereof, or any other means, methods and apparatus allowing to maintain the body-contacting layer 22 in contact with the outer layers 26.

It will hence be readily understood that the hood-shaped structure 21 may comprise any number of outer layers 26 (i.e., a first outer layer 26*a*, a second outer layer 26*b*, and the like) required to ensure sufficient mechanical and thermal resistance, while allowing the perspiration process, and that the material(s) forming each layer has(have) to be selected accordingly.

The various embodiments of the firefighter protective hood 20 presented in the current description are compliant to NFPA 1971 (2013 edition) Standard on Protective Ensembles for Structural Fire Fighting and Proximity Fire Fighting. In some implementations, each of the layers are individually tested for flame resistance, heat and thermal resistance, cleaning shrinkage, and burst strength, and the hood composites (i.e., the succession of layer(s) included in the firefighter protective hood) are tested for thermal protective performance.

EXAMPLES

Figure 4A:
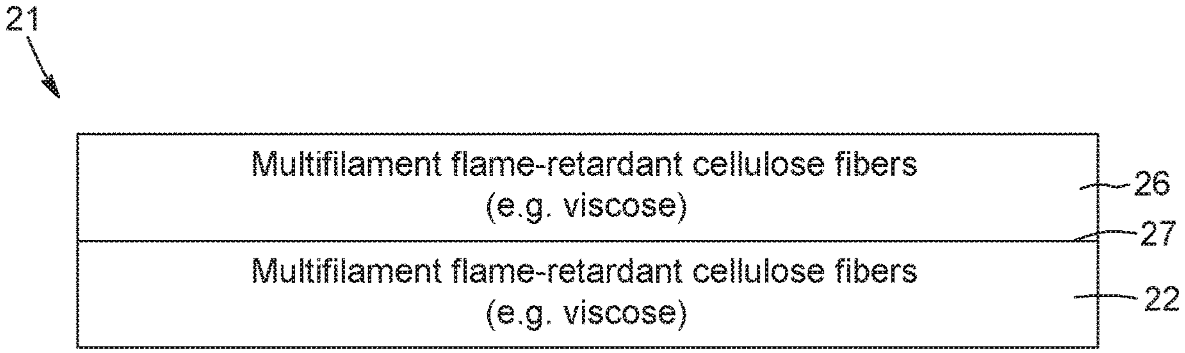
FIGS. 4A and 4B show a schematic cross-sectional view of a hood-shaped structure according to other possible embodiments.

In one example, illustrated in FIG. 4A, the hood-shaped structure 21 comprises two layers:

- The body-contacting layer 22, which is made of a fabric of 100% multifilament flame-retardant cellulose fibers; and
- One outer layer 26 defining an interface 27 with the body-contacting layer 22. The second layer is made of a fabric of 100% multifilament flame-retardant cellulose fibers.

Figure 4B:
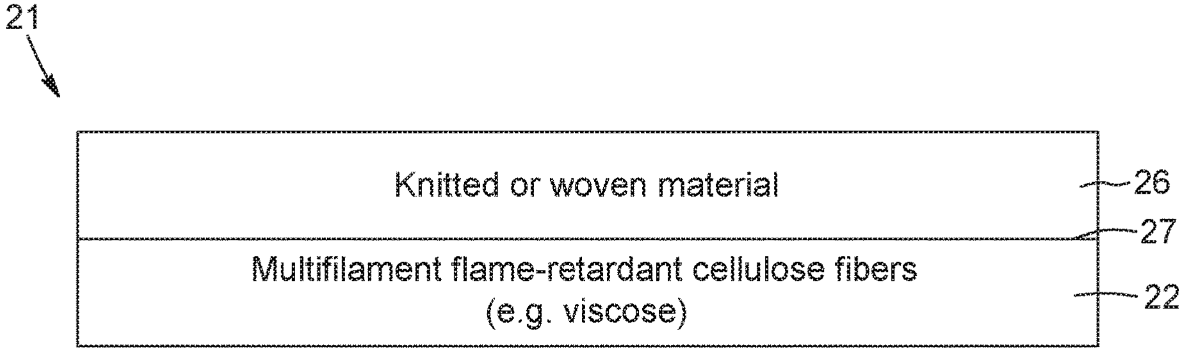

In another example illustrated in FIG. 4B, the hood-shaped structure 21 includes two layers:

- The body-contacting layer 22, which is made of a fabric of 100% multifilament flame-retardant cellulose fibers; and
- One outer layer 26, which is made of a knitted or woven material.

Figure 5A:
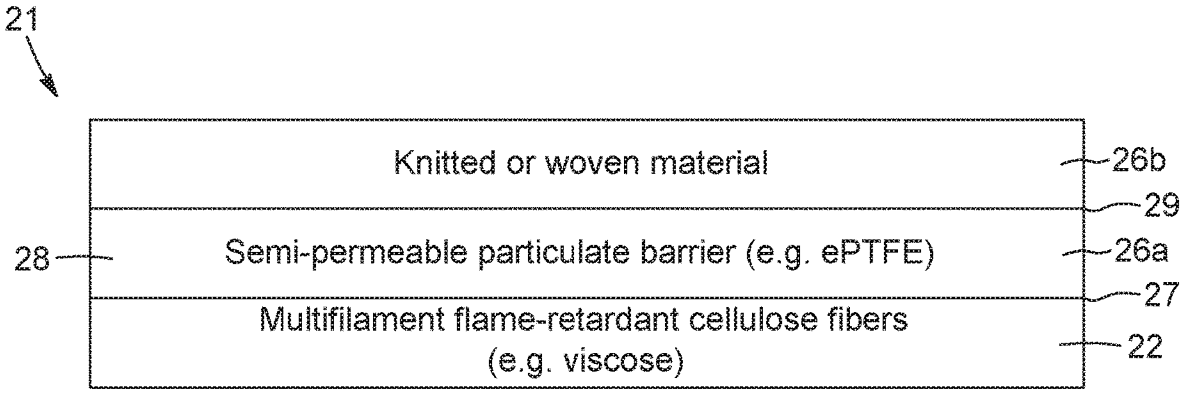
FIGS. 5A to 5E show a schematic cross-sectional view of a hood-shaped structure according to other possible embodiments.

In another example illustrated in FIG. 5A, the hood-shaped structure 21 comprises three layers:

- The body-contacting layer 22, which is made of fabric of 100% multifilament flame-retardant cellulose fibers;
- A first outer layer 26*a*, embodied by the semi-permeable particulate barrier 28, made for example of ePTFE. The first outer layer 26*a* extends over an entirety of the body-contacting layer 22 surface, hence forming a first interface 27 between the body-contacting layer 22 and the first outer layer 26*a*; and
- A second outer layer 26*b*, which is made of a knitted or woven material. The second outer layer 26*b* extends outwardly of an entirety of the first outer layer 26*a* surface, hence forming a second interface 29 between the first and second outer layers 26*a*, 26*b*.

Figure 5B:
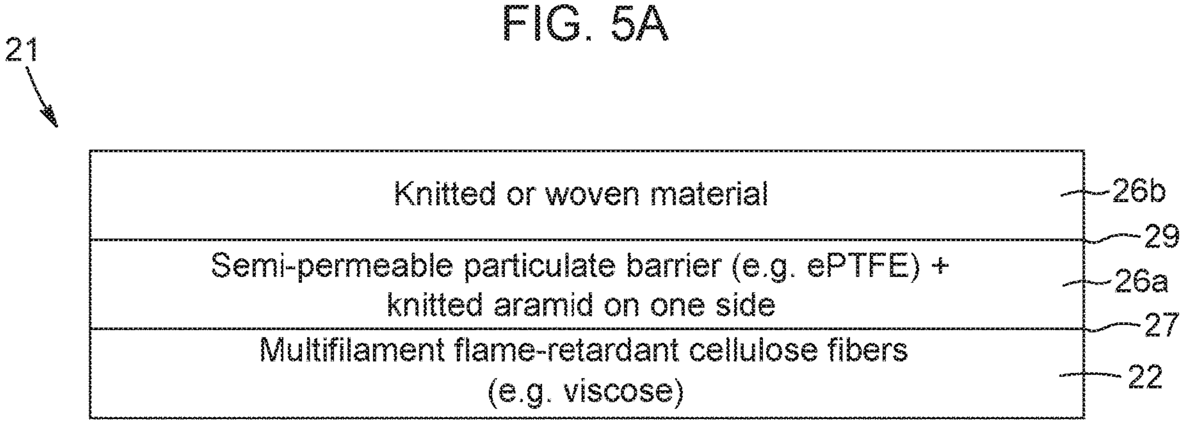

The example illustrated in FIG. 5B includes four layers:

- The body-contacting layer 22 made of multifilament flame-retardant cellulose fibers;
- A first outer layer 26*a*, which is the semi-permeable particulate barrier 28;
- A fabric of an aramid material knitted on one side of first outer layer 26*a*; and
- A second outer layer 26*b*, which is made of a knitted or woven material.

Figure 5C:
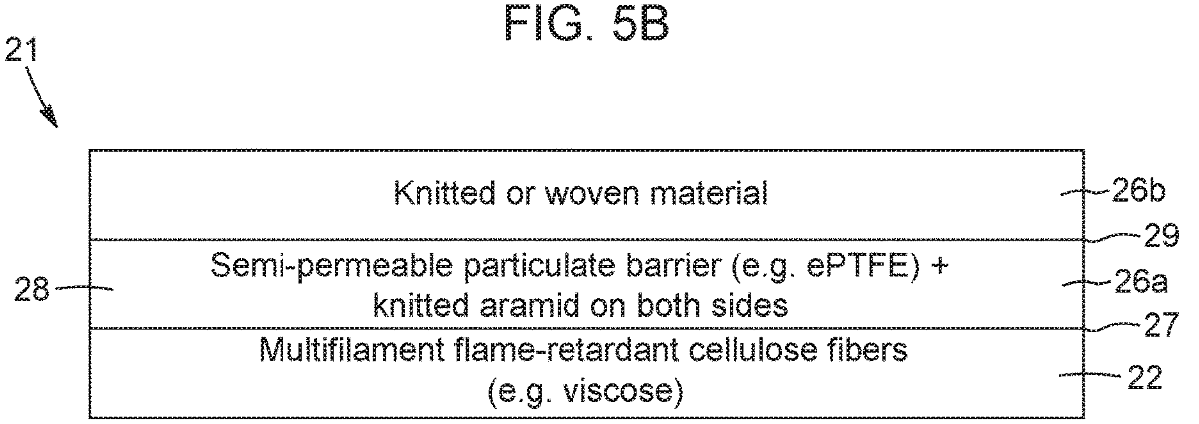

The example illustrated in FIG. 5C includes 5 layers:

- The body-contacting layer 22 made of multifilament flame-retardant cellulose fibers;
- A first outer layer 26*a*, which is the semi-permeable particulate barrier 28;
- Two layers made of a fabric of an aramid material, each being knitted on a respective side of first outer layer 26*a*; and
- A second outer layer 26*b* made of a knitted or woven material.

Figure 5D:
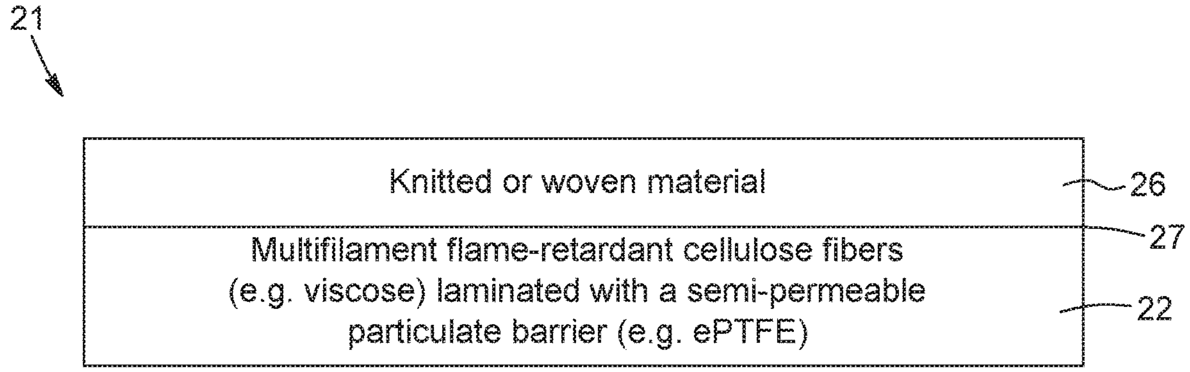

Now referring to FIG. 5D, the hood-shaped structure 21 may include three layers:

- The body-contacting layer 22 made of 100% multifilament flame-retardant cellulose fibers;
- one outer layer 26 made of a knitted or woven material; and
- the semi-permeable particulate barrier 28 made of ePTFE and laminated onto the body-contacting layer 22.

Figure 5E:
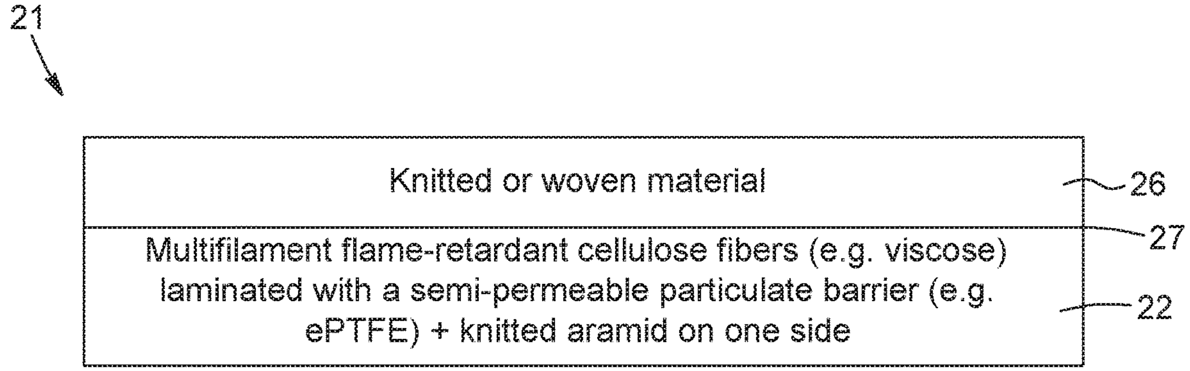

The example illustrated in FIG. 5E includes three layers:

- The body-contacting layer 22 made of multifilament flame-retardant cellulose fibers;
- A fabric made of aramid fibers knitted on one side of the body-contacting layer 22; and
- A fabric made of a knitted or woven material.

Figure 6A:
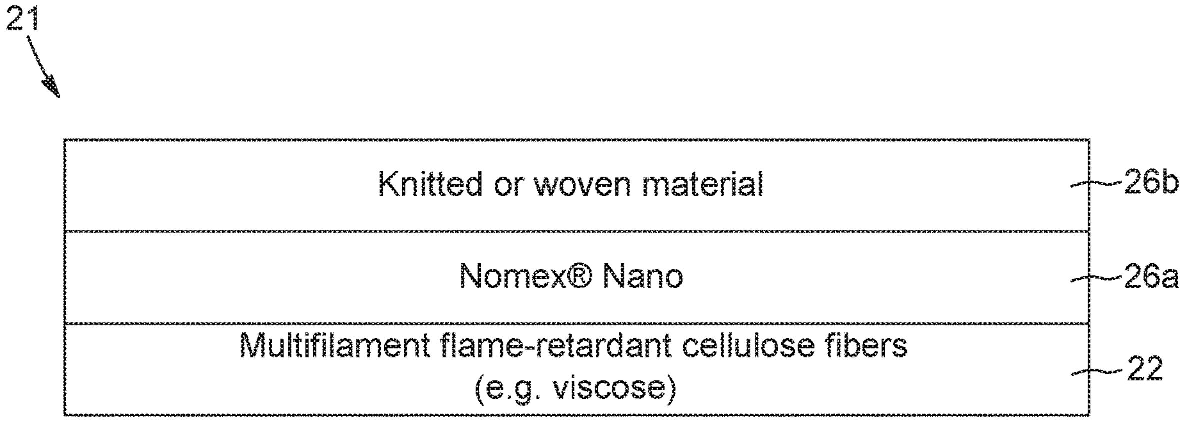
FIGS. 6A to 6C show a schematic cross-sectional view of a hood-shaped structure according to other possible embodiments.

In another example, illustrated in FIG. 6A, the hood-shaped structure 21 includes three layers:

- the body-contacting layer 22 made of a fabric of 100% multifilament flame-retardant cellulose fibers;
- a first outer layer 26*a* defining a semi-permeable particulate barrier 28 made of meta-aramid nanofibers (e.g., Nomex®); and
- a second outer layer 26*b*. The second outer layer 26*b* is made of knitted or woven material.

Figure 6B:
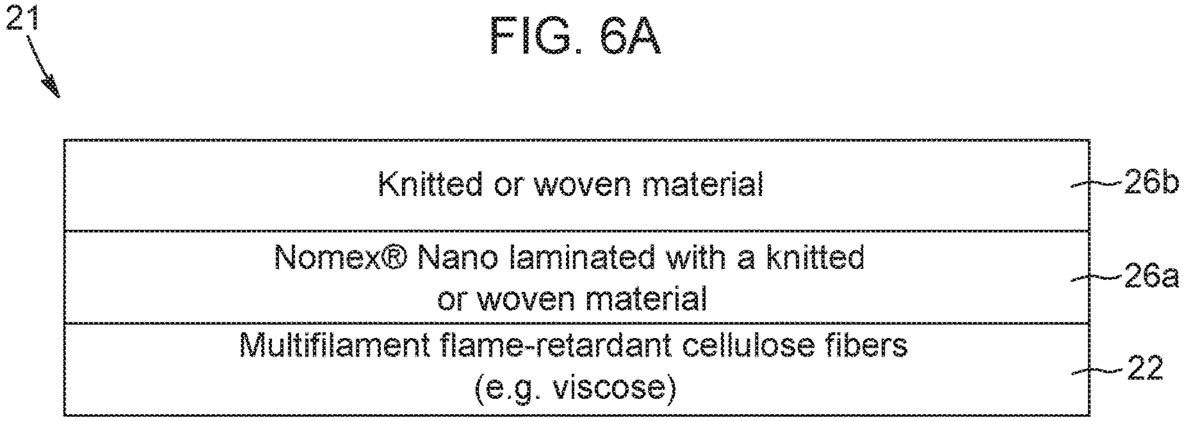

The example illustrated in FIG. 6B includes four layers:

- the body-contacting layer 22 made of a fabric of 100% multifilament flame-retardant cellulose fibers;

- a first outer layer 26*a* defining a semi-permeable particulate barrier made of meta-aramid nanofibers (e.g., Nomex®);
- a second outer layer 26*b*. The second outer layer 26*b* is made of knitted or woven material; and
- an additional layer made of meta-aramid nanofibers material knitted (e.g., Nomex®) to the first outer layer 26*a*.

Figure 6C:
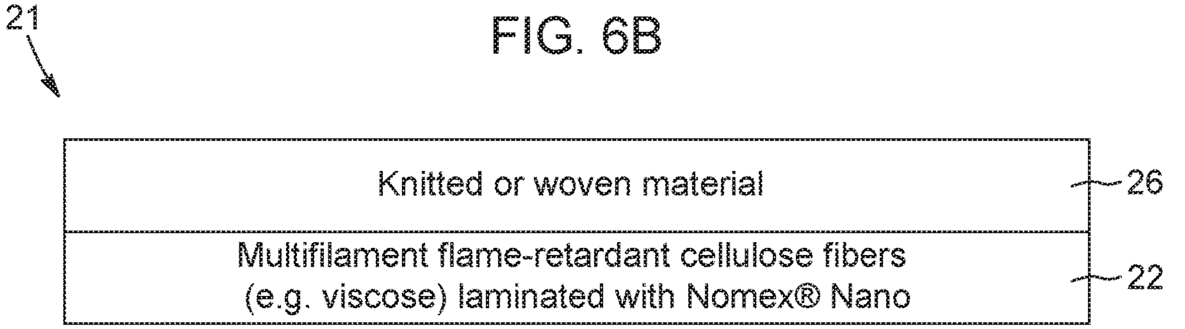

A variant of the embodiment of FIG. 6B is shown in FIG. 6C, in which the additional layer (for example made of Nomex®) is laminated onto body-contacting layer 22.

Firefighter Protective Gloves

Figure 7:
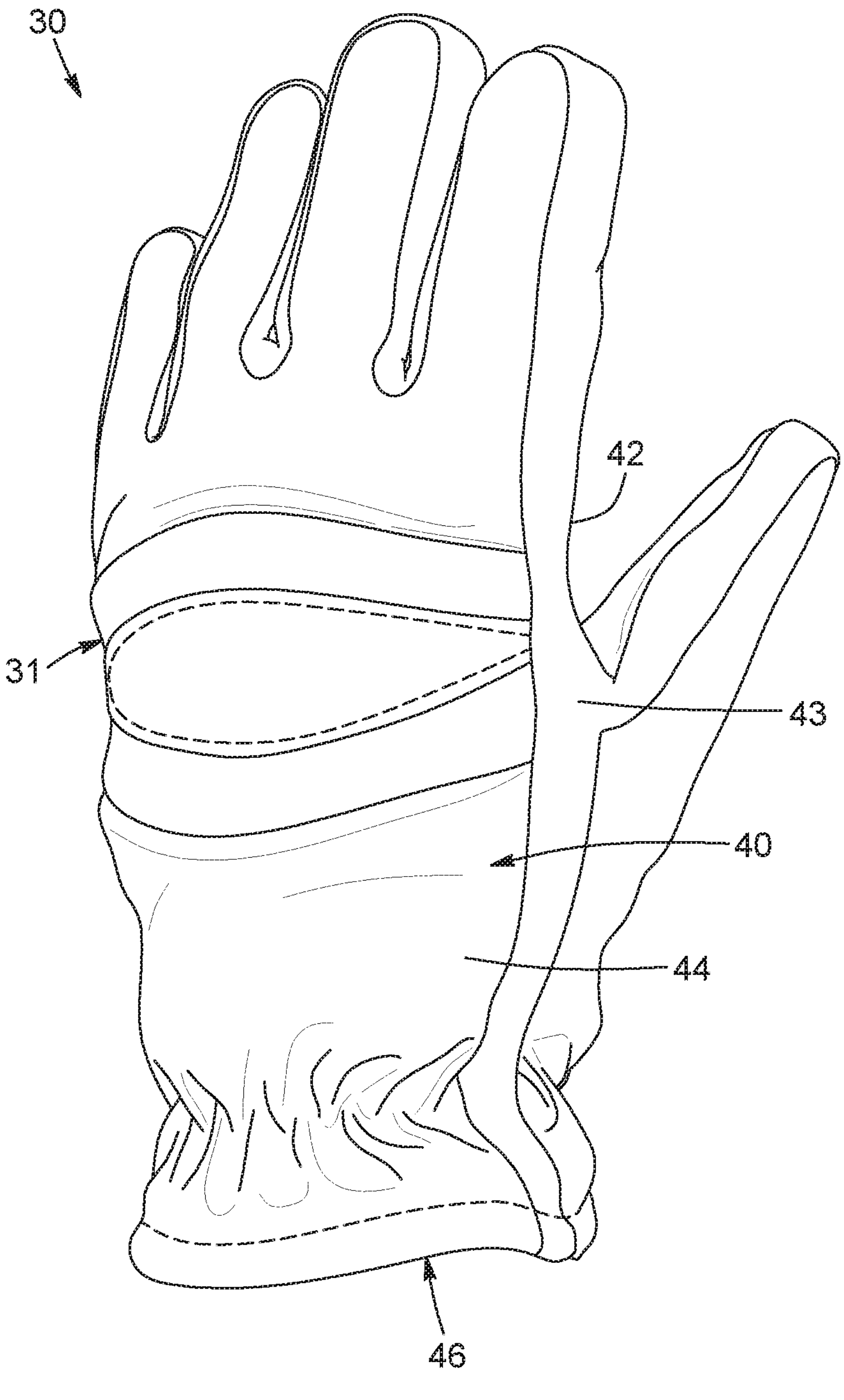
FIG. 7 shows a back-hand side portion of a firefighter protective glove according to an embodiment.
Figure 8:
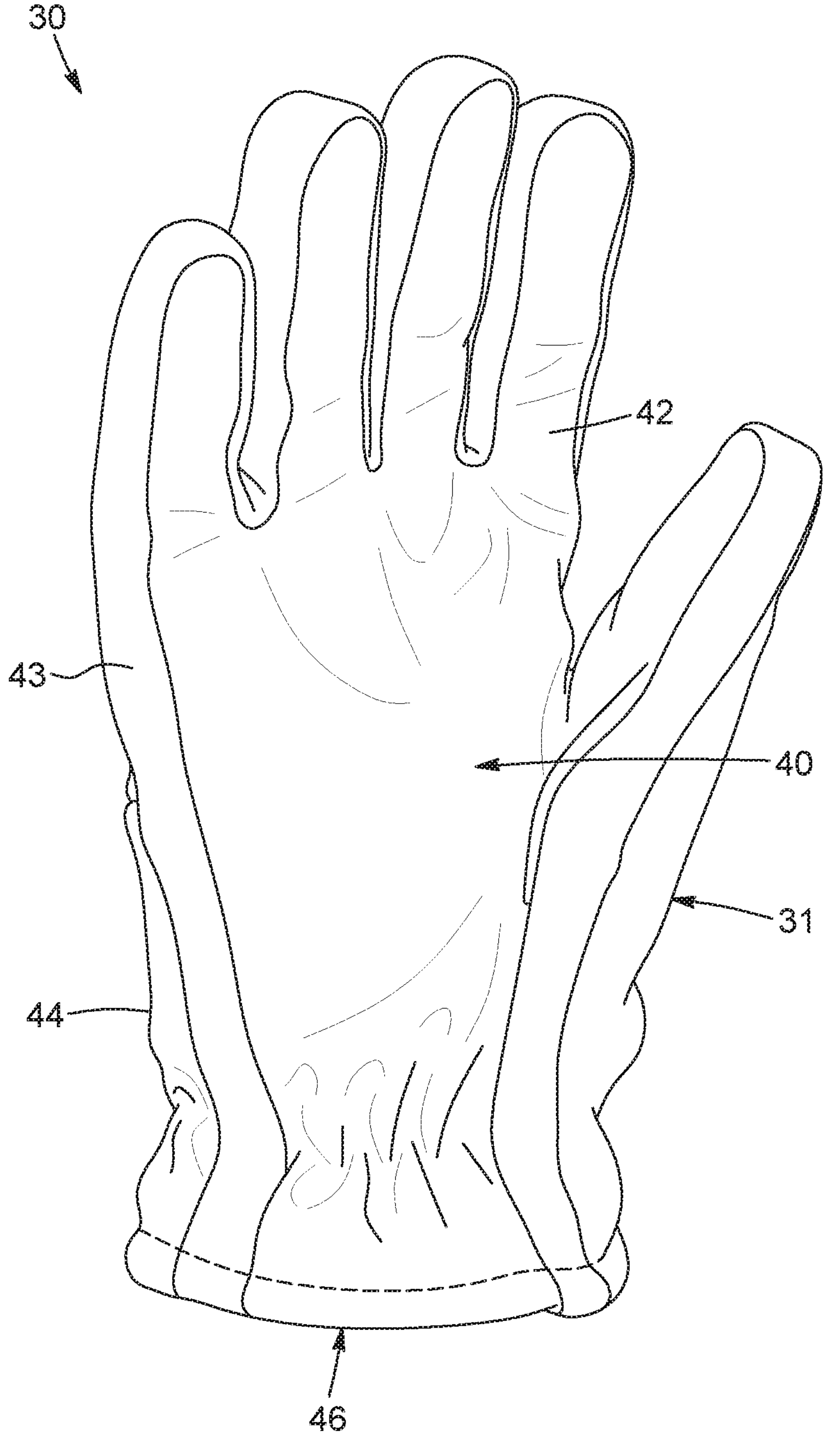
FIG. 8 shows a palm side portion of the firefighter protective glove shown on FIG. 7.
Figure 9:
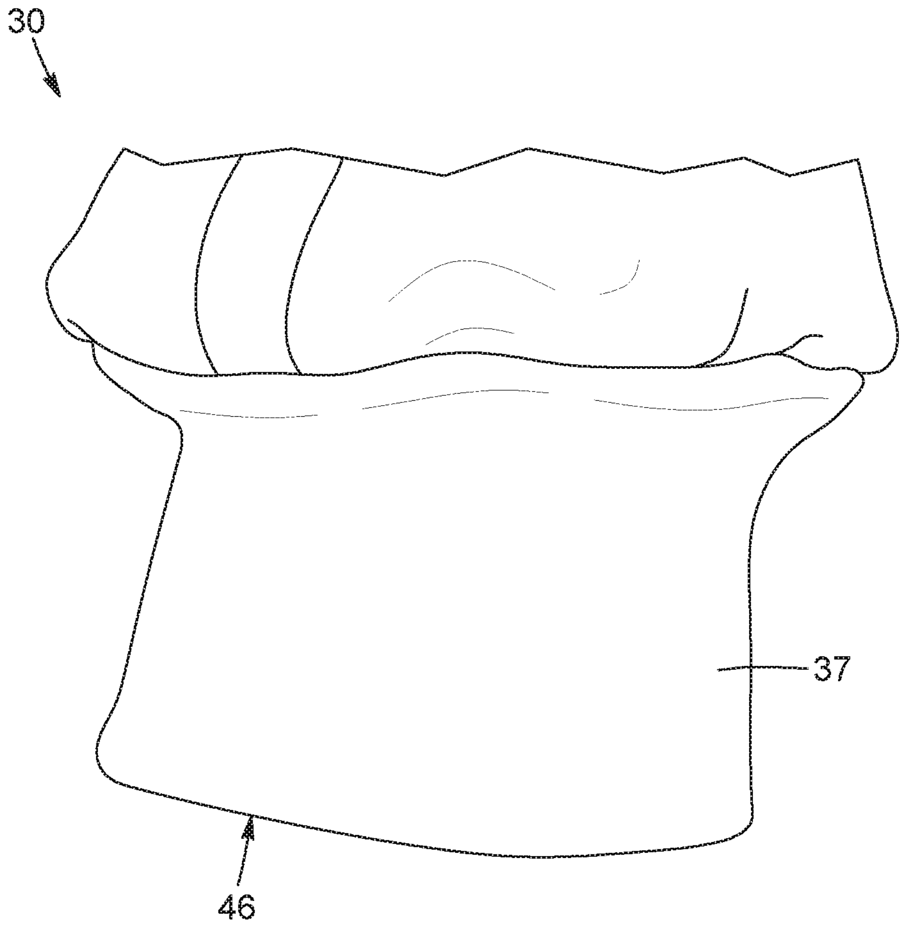
FIG. 9 shows a close-up view of a wrist portion of a firefighter protective glove with a wristlet according to a possible embodiment.

Referring to FIGS. 7 to 9, embodiments of a firefighter protective glove 30 are shown.

Figure 11:
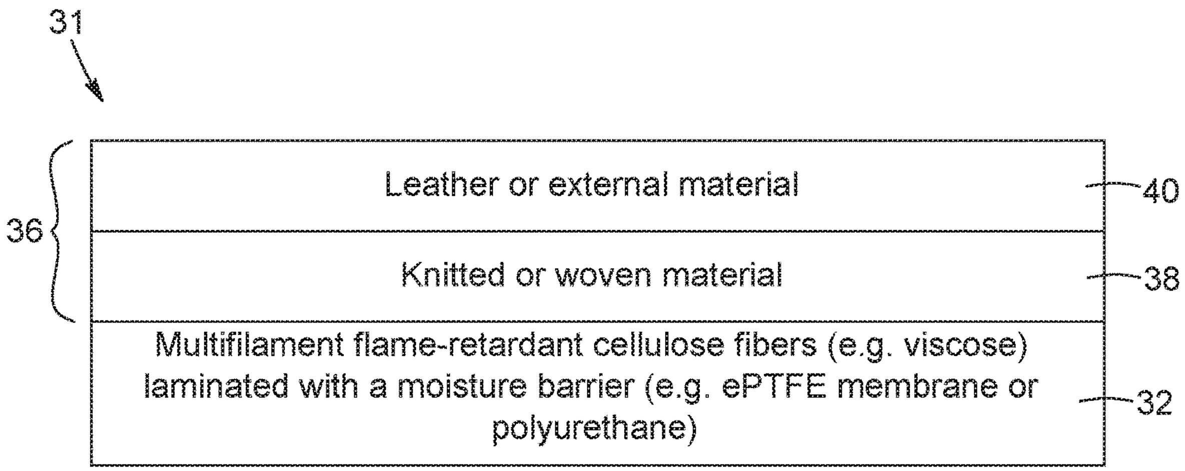
FIG. 11 shows a schematic cross-sectional view of a glove-shaped structure according to another possible embodiment.
Figure 12:
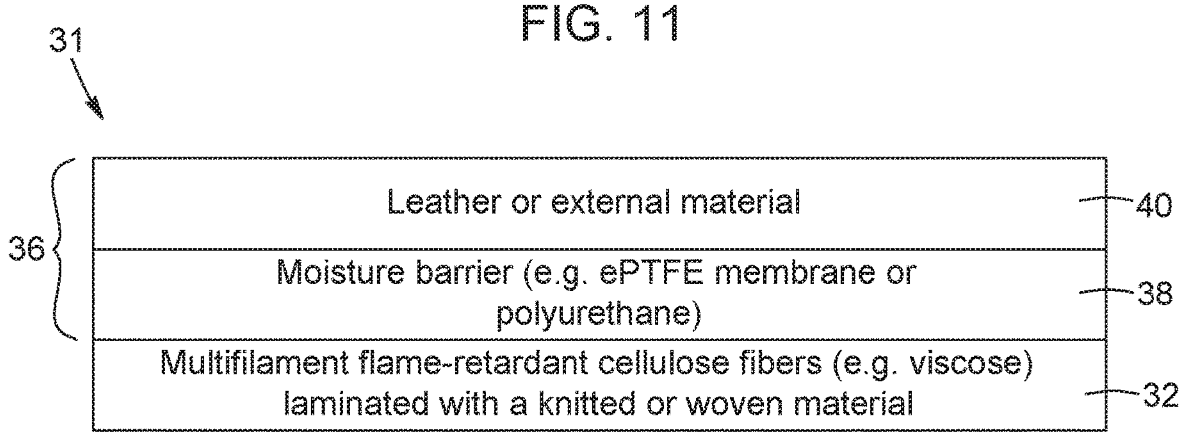
FIG. 12 shows a schematic cross-sectional view of a glove-shaped structure according to another possible embodiment.

The firefighter protective glove 30 includes a glove-shaped structure 31. The glove-shaped structure 31 includes a plurality of superimposed layers (simply referred to as the "superimposed layers"). As it will be described in greater detail below, the superimposed layers include a body-contacting layer 32, a moisture barrier 38 and an outer shell 40 (as illustrated in FIGS. 11 to 13). The moisture barrier 38 and the outer shell 40 will be commonly referred to as the "other layers 36".

As illustrated in FIGS. 7 and 8, the glove-shaped structure 31 includes a palm side portion 42 and a back-hand side portion 44. At least one of the palm side portion 42 and the back-hand portion 44 includes the superimposed layers. In some embodiments, both the palm side portion 42 and the back-hand side portion 44 include the superimposed layers.

In some embodiments, the palm side and the back-hand portions 42, 44 may consist of two distinct pieces to be assembled along their respective perimeter to form the glove-shaped structure 31. Optionally, a fourchette 43 (e.g., a piece of fabric joining to portions of the glove) may be provided between the palm side and the back-hand portions 42, 44 of the glove-shaped structure 31, so that the glove 30 has a tridimensional body when the palm side and the back-hand portions 42, 44 of the glove are joined together by the fourchette.

In some embodiments, the palm side portion 42 and the back-hand portion 44 are each made in one piece, i.e., each one of the palm side portion 42 and the back-hand portion 44 is made from one individual and distinct piece. Optionally, each one of the palm side and back-hand portions 42, 44 could be made of a single-piece of the same material (i.e., the material forming the palm side 42 is the same as the one forming the back-hand portion 42). Alternatively, they could be made in many pieces (e.g., two, three, or more) of the same material, but could also be made of many pieces of different materials comprising one or a combination of material(s) which has/have been previously listed and described, leather and/or a glove moisture barrier The glove-shaped structure 31 includes one hand opening 46. The hand opening 46 may be of such dimensions that it allows the hand or a portion of the hand of the user to be snugly yet tightly inserted into the protective glove 30. Optionally, the hand opening 46 could be reinforced along a portion or an entirety of its perimeter using knitting, weaving, stitching, binding or the like. It may further comprise a band of elastic and/or resilient material to provide further comfort to the user. The firefighter protective glove 30 may further comprise indentation, recess and the like, according to one's need(s) to promote comfort of the user and/or air circulation.

In one embodiment, the firefighter protective glove 30 has a fingers, palm and wrist regions, each respectively covering the fingers, the palms and the wrist of the user, respectively. At least some of the regions may be reinforced so as to increase mechanical resistance using means and methods known by one skilled in the art.

In some embodiments, and referring to FIG. 9, the firefighter protective gloves may comprise a wrist band 37 (also referred to a "wristlet") for additional protection. The wrist band 37 can be made of one or a plurality (e.g., two, three or more) layers of a flame-retardant cellulose fiber selected from the group consisting of: meta-aramids (e.g., Nomex®), para-aramids (e.g., Kevlar®), polybenzimidazole (e.g., PBI®), melamine (e.g., Basofil®), flame-retardant rayon (e.g., P84 Lenzing®), polyacrylonitrile (PAN), carbon and combinations thereof. In some variants, the wrist band 37 could be made from synthetic fiber. Alternatively, the wrist band 37 could also be made from one flexible folded sheet (or portions of sheet) of the previously listed materials, affixed to the wrist region of the protective glove.

Figure 10:
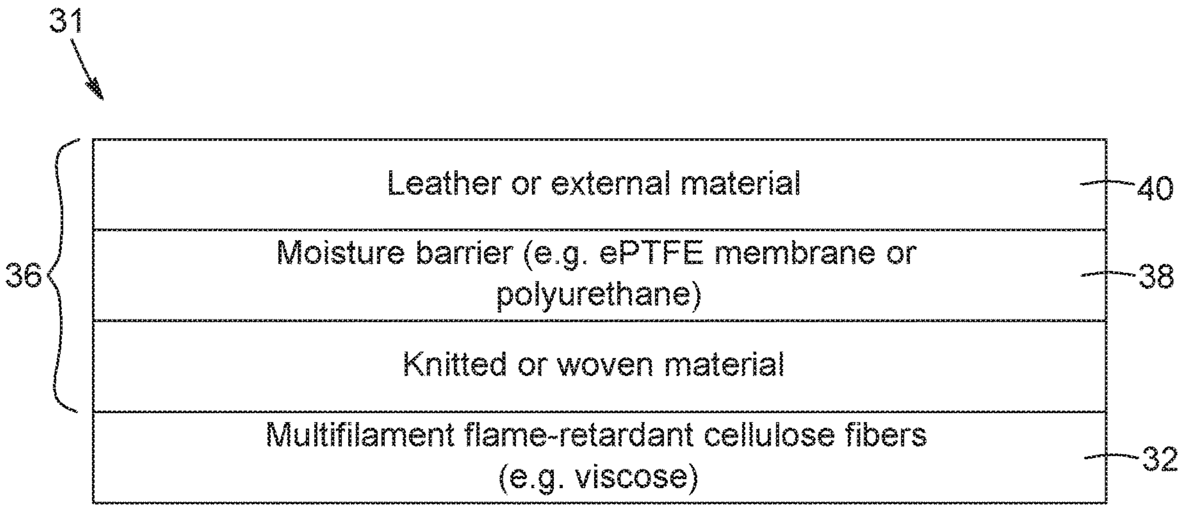
FIG. 10 shows a schematic cross-sectional view of a glove-shaped structure according to another possible embodiment.

Now turning to FIGS. 10 to 12, the superimposed layers include a body-contacting layer 32 made of a fabric of multifilament flame-retardant cellulose fibers. The body-contacting layer 32 defines an innermost one of the superimposed layers. In this sense, the glove-shaped structure 31 is similar to the hood-shaped structure.

The body-contacting layer 32 may be in direct or indirect contact with the body of the wearer, and covers at least portion(s) of specific area of the skin and/or body of the user that need to be mechanically and thermally protected, and allows evaporative cooling. Preferably, the body-contacting layer 32 is in direct contact with a substantial portion of the hand and/or wrist of the user in the areas typically covered by a firefighter glove. However, it will be readily understood that some portions of the body-contacting layer 32 could be indirectly in contact with the body of the user, meaning that there is an intermediate layer between the body-contacting layer 32 and skin and/or body of the user. For example, the body-contacting layer 32 may be in contact with clothes, elements the firefighter protective ensemble and/or any other piece of equipment that may be worn by the user.

As it has been previously mentioned, the glove-shaped structure 31 includes a plurality of superimposed layers (also referred to as the superimposed layers) of which the body-contacting layer 32 is the innermost one. The glove-shaped structure also includes other layers 36. The other layers 36 include at least a moisture barrier 38 and an outer shell 40, as it will be described in greater detail below.

In some embodiments, the other layers 36 extend over an entirety of the body-contacting layer 32, i.e., the other layers and the body-contacting layer 32 form a stack of materials over their respective surface area, and hence define the superimposed layers.

Alternatively, the other layers 36 could extend over a portion of the body-contacting layer 32, so as to expose predetermined areas of the body-contacting layer 32, for example for better cooling of high metabolic heat in specific regions of the user's body.

The body-contacting layer 32 and the other layers 36 have different, yet complementary functionalities. Indeed, the structure and composition of the body-contacting layer 32 are such that they provide comfort to the user and evaporative cooling, while the other layers 36 notably act as thermal and mechanical barriers. Moreover, the body-contacting layer 32 promotes air circulation and may for example be porous. The other layers 36 promote mechanical and thermal resistance, and may further comprise air-permeable knits. The combination of such layers (i.e., the superimposed layers) allows maintaining relatively high perspiration transmission and evaporation, while exhibiting substantially good thermal and mechanical properties.

In some embodiments, the body-contacting layer 32 is made of a fabric including multifilament flame-retardant cellulose fibers, such as the one which have been previously listed with respect to the description of the protective hood. It is to be noted that the cellulose fibers may be regenerated.

In one embodiment, the body-contacting layer 32 is 100% made of flame-retardant multifilament cellulose fibers. Optionally, the cellulose fibers may contain a small amount of short staple fibers spun into a yarn, instead of filament fibers. For instance, the body-contacting layer 32 may include up to about 25% of other constituents, such as meta-aramids (e.g., Nomex®), para-aramids (e.g., Kevlar®), polybenzimidazole (PBI®), melamine (e.g., Basofil®), polyamide (e.g., P84®), polyacrylonitrile (PAN), or carbon fibers. As it has been previously mentioned with respect to the protective hood, a body-contacting layer including up to about 25% of other constituents (i.e., materials different than flame-retardant filament cellulose fibers) will be also referred to as being made of flame-retardant filament cellulose fibers.

The body-contacting layer 32 may either be made of knitted or woven fabric. It will be understood that the body-contacting layer 32 can be knitted, woven, intertwined, braided, or obtained by any other means and methods allowing creating fabric.

In some embodiments, the fabric of flame-retardant cellulose fibers includes multifilament fibers or yarns. For example, the body-contacting layer 32 could be a knitted fabric formed of 100% multifilament cellulose fibers, the cellulose fibers being selected from the list of materials which have been previously presented.

In some embodiments, the cellulose fiber is a rayon fiber, and the rayon fiber is a viscose fiber.

As it has been briefly introduced, the superimposed layers include other layers 36, which in turn include a moisture barrier 38 similar to the one found in the firefighter protective hood 20. The moisture 38 found in the glove 30 also prevents liquid chemicals and/or water from reaching the body. It may be impermeable to particulate(s) having a diameter of about or greater than 1 micrometer, while being permeable to water and/or water vapors. It will be understood that the function of the moisture barrier 38 is to promote air circulation and evaporative cooling, while blocking at least some or every particulate(s) that may be harmful to the user, such as cancerous or toxic particulates. The moisture barrier 38 also acts as a water barrier to limit the passage of water towards an interior portion of the firefighter protective glove 30.

In one embodiment, the moisture barrier 38 is made of expanded polytetrafluoroethylene (ePTFE).

In one embodiment, the moisture barrier 38 is laminated to the body-contacting layer 32 and/or another one of the other layers 36. As such, the moisture barrier 38 is stacked ("sandwiched") between the body-contacting layer 32 and one of the other layers 36. Alternatively, the moisture barrier 38 could be affixed to the body-contacting layer 32 using means and methods which have been previously described.

In some embodiments, the moisture barrier 38 is made from a material selected from the group consisting of: spun yarns, multifilament yarns and combinations of spun and multifilament yarns.

In other embodiments, the moisture barrier 38 is made of expanded polytetrafluoroethylene (ePTFE). Alternatively, the moisture barrier 38 is made of polyurethane.

As it has been previously mentioned, the plurality of superimposed layers includes other layers 36 which notably include an outer shell 40. The outer shell 40 extends over the moisture barrier 38. While the outer shell 40 defines an outermost one of the plurality of superimposed layer, an intermediate layer could alternatively be provided between the outer shell 40 and the moisture barrier 38, and so the outer shell 40 may extend over another layer 36 which is different than the moisture barrier 38. The outer shell 40 acts as a thermal and mechanical barrier for the hand(s) of the user. As such, the outer shell 40 corresponds to the one of the other layers 36 in contact with the outer environment (i.e., an outermost layer of the glove).

The outer shell 40 may be made of a material selected from the group consisting of: leather, knitted fabric, woven fabric, meta-aramids (e.g., Nomex®), para-aramids (e.g., Kevlar®), polybenzimidazole (e.g., PBI®), melamine (e.g., Basofil®), flame-retardant rayon (e.g., P84 Lenzing®), and combinations thereof. It will be understood that the palm side and the back-hand portions 42, 44 are made of a material that enhance heat and slash protection for the hands of the user, while exhibiting good dexterity to perform manual tasks.

It will be readily understood that the firefighter protective glove 30 may comprise any number of layers required to ensure sufficient mechanical and thermal properties, while allowing the perspiration process, and that the material(s) forming each layer has(have) to be selected accordingly. More particularly, body-contacting layer 32 promotes air circulation and may for example be porous. The outer shell 40 (i.e. the layer in contact with the outer environment) promotes mechanical and thermal resistance, and comprises air-permeable knits.

In some embodiments, the outer shell 40 is made from a material selected from the group consisting of: spun yarns, multifilament yarns and combinations of spun and multifilament yarns. In other embodiments, the outer shell 40 is made of a leather.

The various embodiments of the firefighter protective glove 30 presented in the current description are compliant to NFPA 1971 (2013 edition) Standard on Protective Ensembles for Structural Fire Fighting and Proximity Fire Fighting. Individual layers are tested for flame resistance, heat and thermal resistance, cleaning shrinkage, and burst strength, while glove composites are tested for thermal protective performance, More generally, it will be understood that the firefighter protective glove 30, similarly to the protective hood 20, should be thermally and mechanically resistant. The firefighter protective gloves 30, by virtue of their composition and disposition, allow for better heat and slash protection, and so are more resistant from a mechanical point of view.

EXAMPLES

In one example, illustrated in FIG. 10, the glove-shaped structure 31 comprises four layers:

The body-contacting layer 32, made of 100% multifilament flame-retardant regenerated cellulose fibers;

A fabric made of a knitted or woven material;

The moisture barrier 38, made of ePTFE or polyurethane; and

The outer shell 40, made of leather.

In another example, illustrated in FIG. 11, the glove-shaped structure 31 also comprises four layers:

The body-contacting layer 32, made of 100% multifilament flame-retardant regenerated cellulose fibers;

The moisture 38, made of ePTFE or polyurethane, laminated to the body-contacting layer 32;

A fabric made of knitted or woven material; and

The outer shell 40, made of leather.

In another example, illustrated in FIG. 12, the glove-shaped structure 31 also comprises four layers:

The body-contacting layer 32, made of 100% multifilament flame-retardant regenerated cellulose fibers;

A fabric made of a knitted or woven material laminated to the body-contacting layer 32;

The moisture barrier 38; and

The outer shell 40, made of leather.

It will be understood that the palm side portion 42 and the back-hand portion 44 could either be made from the same or a different number of layers. For example, the palm side and the back-hand portions 42, 44 could comprise the same number of layers, and each corresponding layer (e.g., the innermost layer, the first outer layer, the outermost layer, etc.) could be made from the same material, i.e., that the material forming the innermost layer (the body-contacting layer 32) of the palm side portion 42 and of the innermost layer back-hand side portion 44 is the same.

Advantageously, the embodiments of the firefighter protective hood and firefighter protective glove disclosed in the present description have characteristics that provide firefighters with a protective hood and glove which can be easier to don, to align and to doff. The protective hood and glove may also feel cooler on the skin, while providing superior perspiration absorption and transmission, as compared to existing firefighter hoods and gloves. While the protective hood and gloves disclosed in the present description are mostly intended to firefighters needs, it may also be useful for other emergency workers. Indeed, as the protective hood and the protective glove cover respective portions of the user's body, and that the layer of the protective hood or protective glove that is closest to the skin of the wearer can be, in some embodiments, a knit including 100% multifilament flame-retardant yarns derived from regenerated cellulose fibers, it may be particularly useful to anyone who would require a protective element to be used in hazardous situations, such as first responders or the like.

A first advantage of embodiments of the hoods and gloves of the present description concerns ease of use. Contrary to typical protective hoods or gloves, which are made of spun yarn, embodiments of the protective garments described herein slide easily over head, facial hair, the upper-body garment, or the hands of the user, making donning, doffing and alignment of the protective element easier and less time-consuming.

A second advantage of embodiments of the hoods and gloves of the present description concerns comfort. Indeed, protective hoods and gloves according to implementations described herein are advantageous, because the hoods and gloves each includes a body-contacting layer made of a fabric of multifilament flame-retardant cellulose fibers offer good perspiration-transmission (wicking) characteristics, which leads to more efficient evaporative-cooling of the user.

A third advantage of embodiments of the hoods and gloves of the present description concerns the optimization of the protection while maintaining sufficient perspiration evaporation. It is known that an additional layer, such as the ones acting as a moisture barrier, could further be used in protective hoods or protective gloves as a particulate-barrier, which could be particularly useful to protect the user from dangerous particulates. However, such moisture barriers, while used in combination with standard fabrics, may not offer enough total heat loss to meet the requirements of NFPA 1971, 2018 (under development). The moisture barrier is known to also typically increase the thermal insulation of the user, hence decreasing perspiration transport and evaporation. The inclusion of the body-contacting layer as described herein allows mitigating the challenge of providing adequate evaporative cooling and sufficient protection for the user.

A fourth advantage of embodiments of the hoods and glove of the present description concerns the optimization of the protection and durability, while maintaining sufficient perspiration evaporation. The inclusion of the body-contacting layer according to the present description allows mitigating the challenges associated with providing adequate protection against carcinogen particulates, while offering sufficient durability.

Of course, numerous modifications could be made to the embodiments described above without departing from the scope of the appended claims

The invention claimed is:

1. A firefighter protective hood comprising:

a hood-shaped structure comprising a plurality of superimposed layers, the plurality of superimposed layers comprising:

a body-contacting layer made of a fabric of multifilament flame-retardant cellulose fibers and defining an innermost one of the plurality of superimposed layers, wherein the body-contacting layer is porous, the fabric having a porosity and wicking characteristics promoting evaporative cooling of a user when the firefighter protective hood is worn by the user, the fabric comprising:

a first type of fibers, the first type of fibers being multifilament flame-retardant cellulose fibers, the multifilament flame-retardant cellulose fibers comprising yarns with more than one filament running a whole length of the yarns; and a second type of fibers, the second type of fibers being selected from the group consisting of meta-aramids, para-aramids, polybenzimidazole, melamine, polyamide, polyacrylonitrile and carbon fibers; and at least one outer layer extending over at least a portion of the body-contacting layer, wherein the fabric includes at least 75% by weight of the first type of fibers and up to 25% by weight of the second type of fibers, wherein the fabric comprises more than 0% of the second type of fibers.

2. The firefighter protective hood of claim 1, wherein the multifilament flame-retardant cellulose fibers are rayon fibers.

3. The firefighter protective hood of claim 2, wherein the rayon fibers are viscose fibers.

4. The firefighter protective hood of claim 1, wherein the at least one outer layer is made from a material selected from the group consisting of: spun yarns, multifilament yarns and combinations of spun and multifilament yarns.

5. The firefighter protective hood of claim 1, wherein the at least one outer layer comprises a particulate barrier, the particulate barrier being configured to block particulates having a diameter of 1 micrometer or more.

6. The firefighter protective hood of claim 5, wherein the particulate barrier is laminated with the body-contacting layer.

7. The firefighter protective hood of claim 5, wherein the particulate barrier is made of expanded polytetrafluoroethylene.

8. The firefighter protective hood of claim 5, wherein the particulate barrier is made of meta-aramid nanofibers.

9. The firefighter protective hood of claim 1, wherein the firefighter protective hood is compliant to NFPA 1971 (2013 edition) Standard on Protective Ensembles for Structural Fire Fighting and Proximity Fire Fighting.

10. The firefighter protective hood of claim 1, wherein said at least one outer layer comprises a layer made of a fabric of multifilament flame-retardant cellulose fibers.

11. The firefighter protective hood of claim 1, wherein said at least one outer layer comprises a layer made of a knitted or woven material.

12. The firefighter protective hood of claim 1, wherein said at least one outer layer comprises:

a first outer layer comprising a semi-permeable particulate barrier; and a second outer layer extending over an entirety of the first outer layer, the second outer layer being made of a knitted or woven material.

13. The firefighter protective hood of claim 1, wherein said at least one outer layer comprises:

a first outer layer comprising a semi-permeable particulate barrier;

a second outer layer made of an aramid material knitted on one side of the first outer layer; and a third outer layer extending over the first outer layer or the second outer layer, the third outer layer being made of a knitted or woven material.

14. The firefighter protective hood of claim 1, wherein said at least one outer layer comprises:

a first outer layer comprising a semi-permeable particulate barrier;

a second outer layer made of an aramid material knitted on one side of the first outer layer;

a third outer layer made of an aramid material knitted on another side of the first outer layer; and a fourth outer layer extending over the second outer layer or the third outer layer, the third outer layer being made of a knitted or woven material.

15. The firefighter protective hood of claim 1, wherein said at least one outer layer comprises:

a first outer layer comprising a semi-permeable particulate barrier laminated to the body-contacting layer; and a second outer layer extending over the first outer layer, the second outer layer being made of a knitted or woven material.

16. The firefighter protective hood of claim 1, wherein said at least one outer layer comprises:

a first outer layer comprising a semi-permeable particulate barrier laminated to the body-contacting layer;

a second outer layer comprising a fabric made of aramid fibers knitted on one side of the body-contacting layer; and a third outer layer extending over the first outer layer or the second outer layer, the third outer layer comprising a fabric made of a knitted or woven material.

17. The firefighter protective hood of claim 1, wherein said at least one outer layer comprises:

a first outer layer comprising a semi-permeable particulate barrier made of meta-aramid nanofibers; and a second outer layer extending over the first outer layer, the second outer layer being made of a knitted or woven material.

18. The firefighter protective hood of claim 1, wherein said at least one outer layer comprises:

a first outer layer comprising a semi-permeable particulate barrier, the semi-permeable particulate barrier being made of meta-aramid nanofibers;

a second outer layer comprising a fabric made of meta-aramid laminated to the first outer layer; and a third outer layer extending over the second outer layer, the third outer layer being made of a knitted or woven material.

19. The firefighter protective hood of claim 1, wherein said at least one outer layer comprises:

a first outer layer laminated to the body-contacting layer, the first outer layer comprising a semi-permeable particulate barrier made of meta-aramid nanofibers;

a second outer layer laminated to the first outer layer, the second outer layer comprising a fabric made of meta-aramid; and a third outer layer extending over the second outer layer, the third outer layer being made of a knitted or woven material.

20. The firefighter protective hood of claim 1, wherein the multifilament flame-retardant cellulose fibers are regenerated fibers.

21. The firefighter protective hood of claim 1, wherein the body-contacting layer has a low dynamic load, such that the body-contacting layer is adapted to slide over the user's head.

22. The firefighter protective hood of claim 1, wherein the wicking characteristics are selected from the group consisting of: a surface area of the fabric, a thickness of the fabric, materials used in the fabric, a size of perforations present in the fabric and a density of yarns of the fabric.

23. The firefighter protective hood of claim 1, wherein the fabric comprises 75% by weight of the first type of fibers and 25% by weight of the second type of fibers.

* * * * *